United States Patent
Feine

(10) Patent No.: US 8,585,404 B2
(45) Date of Patent: Nov. 19, 2013

(54) EFFICIENCY-MODULATED ULTRASONIC INSTRUMENT INSERTS

(76) Inventor: James S. Feine, Bellaire, TX (US)

(*) Notice: Subject to any disclaimer, the term of this patent is extended or adjusted under 35 U.S.C. 154(b) by 0 days.

(21) Appl. No.: 13/166,485

(22) Filed: Jun. 22, 2011

(65) Prior Publication Data

US 2011/0250559 A1   Oct. 13, 2011

Related U.S. Application Data

(60) Division of application No. 11/161,743, filed on Aug. 15, 2005, now abandoned, which is a continuation-in-part of application No. 10/065,991, filed on Dec. 7, 2002, now abandoned.

(60) Provisional application No. 60/340,575, filed on Dec. 7, 2001.

(51) Int. Cl.
   *A61C 1/07*    (2006.01)

(52) U.S. Cl.
   USPC .............................. 433/119; 433/86

(58) Field of Classification Search
   USPC ............. 433/86, 118, 119, 141–165; 604/22; 606/169, 178; 310/316.01, 26; 601/2–3; 73/1.82; 318/18
   See application file for complete search history.

(56) References Cited

U.S. PATENT DOCUMENTS

| | | | | |
|---|---|---|---|---|
| 5,899,693 A | * | 5/1999 | Himeno et al. | 433/119 |
| 5,980,251 A | * | 11/1999 | Sullivan et al. | 433/119 |
| 6,164,968 A | * | 12/2000 | Feine | 433/119 |
| 6,489,695 B1 | * | 12/2002 | Wun-Fogle et al. | 310/26 |
| 6,494,714 B1 | * | 12/2002 | Copeland | 433/86 |
| 2002/0057156 A1 | * | 5/2002 | Czimmek | 336/30 |
| 2005/0244788 A1 | * | 11/2005 | Feine | 433/165 |
| 2007/0148618 A1 | * | 6/2007 | Feine | 433/119 |

* cited by examiner

*Primary Examiner* — Yogesh Patel
(74) *Attorney, Agent, or Firm* — Daniel N. Lundeen; Lundeen & Lundeen PLLC

(57) ABSTRACT

Efficiency-modulated ultrasonic dental inserts (12) are disclosed for preventing the overpowering of power-sensitive tips (18). The inserts (12) are useful in a handpiece (10) having an induction coil (20) disposed about a well and operable with an adjustable power supply having a maximum power output setting. An efficiency-modulated magnetostrictive element (14) is adapted to be received in the well. A velocity transducer (16) has proximal and distal ends. The proximal end is attached to a distal end of the magnetostrictive element (14). A power-sensitive tip (18) has a proximal end secured to the distal end of the velocity transducer (16). The efficiency of the magnetostrictive element (14) is matched with the power range of the tip (18) to prevent overpowering the tip (18) at the maximum power output setting.

16 Claims, 4 Drawing Sheets

EFFICIENCY-MODULATED ULTRASONIC INSTRUMENT INSERTS

CROSS REFERENCE TO RELATED APPLICATIONS

This application is a divisional application of my earlier U.S. Ser. No. 11/161,743 filed Aug. 15, 2005, abandoned, which is a continuation-in-part U.S. Ser. No. 10/065,991 filed Dec. 7, 2002, abandoned, and claims the benefit of provisional application U.S. Ser. No. 60/340,575 filed Dec. 7, 2001.

BACKGROUND OF INVENTION

This invention relates to ultrasonic instrument inserts, more particularly, to magnetostrictive inserts for ultrasonic dental instruments, and especially to such inserts that are power-matched to the power range of a power-sensitive tip.

Ultrasonic instruments such as dental scalers are well known. The ultrasonic scalers include a generator that electrically induces the scaling tip to vibrate at a very high rate. An alternating current is passed through an induction coil in a handpiece that induces vibration of the magnetostrictive element of an insert in the handpiece. The vibration is transmitted to the tip by a velocity transducer on the end of the magnetostrictive element. The vibration may cause the tip to move elliptically, in a curved linear fashion, or in a "figure eight" pattern.

Some tips operate at a lower frequency, while other tips operate at a higher one. The tip, for example, may vibrate 25,000 times per second (25 KHz). If a tip is connected to an insert and used with a generator and handpiece that operate at the improper frequency or power output, the tip may not operate correctly, or can break during operation.

Many current inserts are employed with new special-use tips that are relatively thin compared to conventional thicker tips. The thickness of the tip and the ultrasonic power setting used will affect the vibration of the tip. Generally, a lower power should be used to vibrate thinner tips, and a higher power used with thicker tips. Unless modulated in some manner, usually by manually adjusting a power setting control such as a knob connected to a potentiometer, the ultrasonic power required to vibrate the thicker tips can overstress the thinner tips, creating metal fatigue and causing tip breakage, sometimes within a matter of seconds. Other special-use tips may vibrate excessively at the typical maximum ultrasonic power levels, making them difficult for the dental practitioner to use, and/or causing patient discomfort. Manufacturers typically recommend a power output setting at less than full power, e.g. 50% or 25% of maximum, for these relatively thinner or special-use tips. Ultrasonic tips labeled with manufacturer-recommend reduced-power settings or which are otherwise commonly used at reduced power settings are collectively referred to herein as "power-sensitive tips." These power-sensitive tips are used in inserts that generally require a minimum or threshold power input before vibration will begin. Above the threshold, the magnitude of the vibration generally increases proportionally with the power supplied. At some point, however, the power input will become excessive in that a sharp increase from the normally linear stress-strain curve for the material of the tip will occur, resulting in accelerated failure of the tip, and/or in that the tip becomes difficult to use or begins to cause patient discomfort. The range of power input from the threshold to the point just before the power input becomes excessive is referred to herein as the "power range" of a particular tip.

Manufacturers and dental practitioners skilled in the art can readily determine the power sensitivity of tips, and the approximate power range in which a specific tip is operable by determining the stress-strain curve and/or by trial and error. Generally, a power sensitive tip is attached to an ultrasonic handpiece comprising a conventional magnetostrictive element connected to a power supply, and operated at increasing levels of power output, from initial tip vibration until metal fatigue, tip breakage, operational difficulty, patient discomfort, or the like occurs. Using this technique, manufactures and users are readily able to determine the minimum and maximum power setting, for which a tip is operable, referred to herein as the "power range." To avoid overpowering power-sensitive tips, their manufacturers may recommend to the operators to use only a lower power setting on the ultrasonic generator unit, such as half power or less. Manufacturers of ultrasonic power supplies generally provide operating instructions suggesting a power setting limit for a specific tip based on the power conversion efficiency of a conventional magnetostrictive element. These guidelines are intended to prevent overpowering of the tip and resultant metal fatigue, tip breakage, operational difficulty and patient discomfort. This has been only partially effective due to operator error, for example the operator may not remember to reduce the power setting before use, as well as complications due to the variations in the numerous makes and models of many manufacturers and the differences in the circuitry of their ultrasonic dental generators.

The stack material normally used in ultrasonic dental scalers is a form of nickel in the shape of strips or leaves. The nickel can be very pure such as Nickel 33 or Nickel 200, or have other metals or materials alloyed with it to enhance its ultrasonic performance, such as, for example, PERMANICKEL alloy. The surfaces of the nickel strips are typically oxidized to establish a coating, which enhances the ultrasonic efficiency of the strips. The coating also serves to avoid significant variations in efficiency over the useful life of the stack since the surfaces would oxidize at the aqueous conditions of use and autoclave sterilization. As used herein, "nickel" refers to nickel and magnetostrictive nickel alloys, optionally with oxidized surfaces, unless the context indicates otherwise. The stacks made from these optimum materials are usually highly efficient, typically capable of converting 50% or more of the electrical power input to mechanical oscillatory power at the peak resonant frequency, referred to herein as "high-efficiency stacks." The characteristics of "power-sensitive tips" and "power range" as defined above are determined herein as commonly understood in the art, i.e. when the tips are used in an insert with high-efficiency stacks, unless indicated otherwise by context.

An ultrasonic dental instrument, which operates in a manner to achieve peak efficiency and at maximum energy conversion, is known, for example, from U.S. Pat. No. 3,636,947 to Balamuth. Generally, to achieve vibration of the tip, the magnetostrictive element and surrounding components are structured to allow the ultrasonic unit to operate with high efficiency and minimum disruption of power conversion. The device is generally unconcerned with protection of power-sensitive tips, as the efficiency of the magnetostrictive element is optimized independent of the tip used. Generally, there is no method, other than reducing power output of the power supply, e.g. with a manually adjusted potentiometer, to prevent metal fatigue, tip breakage, operational difficulty, patient discomfort, or the like occurring due to tip power-sensitivity.

An apparatus for adjusting the power to an ultrasonic dental insert by use of a control switch is disclosed in U.S. Pat.

No. 3,691,437 to Andersson. The power output of the tool is controlled by a manually operated control switch, which is installed on the outer surface of the dental tool. The control switch causes a short circuit when activated, is similar to reducing the power output at the power supply, and is under the control of the operator. The reduced magnitude of oscillation of the tip is unrelated to tip sensitivity and, therefore does not provide a method of automatically preventing overpowering power-sensitive tips and the concomitant metal fatigue, tip breakage, operational difficulty, or patient discomfort.

SUMMARY OF INVENTION

This invention allows the manufacturer to custom design or adjust the power range of the tip/stack assembly (insert) to match the power range of the power output range of the ultrasonic generator. This allows the full range control of the generator to be used regardless of the tip thickness and/or shape while automatically modulating the power converted to the handpiece/insert when power-sensitive tips are employed to prevent overpowering independently of any operator-adjustable power control. The present invention enables the manufacturer of magnetostrictive ultrasonic dental inserts to design the stack system, usually nickel vibrating elements, to be efficiency modulated to match the operating characteristics of power-sensitive tips.

Generally, the power conversion by the magnetostrictive element is proportional to the amount of magnetostrictive material in the handpiece insert at the peak resonant frequency. The efficiency-modulated magnetostrictive element with specific energy conversion efficiency can be power matched to a power sensitive tip operable in a specific power range of a specific power supply. Thus, operators can use the full range of power adjustment setting of their ultrasonic dental generator as they are accustomed to using with the generally thicker, less sensitive tips, without overstressing the thinner tip and causing premature metal fatigue tip breakage, or otherwise overpowering a power-sensitive tip. Each type or style of tip and frequency used, commonly 25 KHz, 30 KHz or another frequency, can be manufactured with the appropriate efficiency-modulated stack to enable the operator to achieve the full operating life of the insert without inadvertent metal fatigue tip breakage.

As used herein, an "efficiency modulated stack" has a lesser power conversion at the peak resonant frequency than a conventional high-efficiency stack, e.g. less than 50% power conversion in one embodiment. Relative to conventional high-efficiency magnetostrictive elements, which are designed to maximize power conversion efficiency, the efficiency-modulated magnetostrictive element of the present invention has a reduced power conversion efficiency, which can be power matched to a power sensitive tip and power supply. The present invention provides a method of using the full range of power settings of the power supply without the otherwise adverse effects of using the full range of power with a power sensitive tip. Given a specific make and model of a power supply, and a specific make and model of power-sensitive tip, the magnetostrictive element of the present invention is efficiency modulated.

The present invention also provides a moldable nickel particulate-filled stack, e.g. by injection molding, which can be made faster, easier and inexpensively, and which can be disposable, thereby avoiding the need for autoclave sterilization.

In one embodiment, the present invention provides an ultrasonic dental insert useful in a handpiece having an induction coil disposed about a well and operable with an adjustable power supply having a maximum power output setting. The insert includes an efficiency-modulated magnetostrictive element adapted to be received in the well. A velocity transducer has proximal and distal ends, wherein the proximal end is attached to a distal end of the magnetostrictive element. A power-sensitive tip has a proximal end secured to the distal end of the velocity transducer. The efficiency of the magnetostrictive element is matched with a power range of the tip to prevent overpowering the tip at the maximum power output setting.

The efficiency-modulated magnetostrictive element can have an efficiency rating less than 50 percent, i.e. less than 50 percent of the electrical power input at the peak resonant frequency is converted to mechanical oscillatory power. The magnetostrictive element can include nickel.

In one embodiment, the magnetostrictive element can include a plurality of coextensive longitudinally oriented nickel or nickel alloy wires. The wires can be welded at a distal end thereof inside a ring secured to the proximal end of the velocity transducer. The wires can have a uniform cross section, or a non-uniform cross section. The magnetostrictive element can include one or more magnetostrictive-dampening wires. The magnetostrictive element can also include one or more non-magnetostrictive wires, including wires made of a material that diminishes the eddy currents of the magnetostrictive element. The wires can be stiffened by axially spaced containment rings, and can also include a proximal end cap receiving a proximal end of the wires. In an alternate or additional embodiment, the ultrasonic dental insert can further include a containment wire wound around the longitudinal wires.

In one embodiment, the magnetostrictive element includes a void space or spaces as an efficiency modulation device. In other embodiments, the magnetostrictive element comprises a solid nickel rod, a plurality of nested coaxial tubes, or a volume of non-magnetostrictive material as an efficiency modulation device.

One embodiment of the ultrasonic dental insert provides a magnetostrictive element comprising a magnetostrictive particulate-filled polymeric monolith, e.g. epoxy resin, ABS resin, or the like. The polymeric monolith can be interlockingly molded to the velocity transducer or to a headpiece that is releasably attachable to the velocity transducer, for example, by screw threads. The polymeric monolith can be engineered to deform at autoclave sterilization conditions, for example, wherein the polymeric monolith comprises acrylonitrile-butadiene-styrene copolymer.

In another embodiment, the present invention provides an ultrasonic dental insert useful in a handpiece having an induction coil disposed about a well and operable with a power supply. The insert includes a magnetostrictive element adapted to be received in the well. A velocity transducer has proximal and distal ends, wherein the proximal end is attached to a distal end of the magnetostrictive element. A tip has a proximal end secured to the distal end of the velocity transducer. The magnetostrictive element comprises a magnetostrictive particulate-filled polymeric monolith, e.g. epoxy resin, ABS resin, or the like. The polymeric monolith is interlockingly molded to the velocity transducer or to a headpiece that is releasably attachable to the velocity transducer, for example, by screw threads. The polymeric monolith can be engineered to deform at autoclave sterilization conditions, for example, wherein the polymeric monolith comprises acrylonitrile-butadiene-styrene copolymer. The insert can be packaged for distribution in a sterilizable package and sterilized, for example by gamma ray irradiation or gas permeation, e.g. ethylene oxide.

In another embodiment, the present invention provides a method of adjusting the power delivered to an ultrasonic dental insert in a handpiece having an induction coil disposed about a well and operable with an adjustable power supply having a maximum power output setting, wherein the insert comprises a power-sensitive tip. The method includes matching the tip with an efficiency-modulated magnetostrictive element to avoid overpowering the tip at the maximum power output setting, coupling the tip to a velocity transducer operatively associated with the magnetostrictive element to form an insert assembly, inserting the assembly in the well, supplying power to the induction coil, and adjusting the power output up to the maximum power output setting.

The magnetostrictive element can be preassembled with the velocity transducer and tip and the preassembled insert can be packaged in a sterilizable package for sterilization and distribution to dental practitioners. The insert can be engineered for a single-use, preferably including the step of automatically deforming the magnetostrictive element upon heating to autoclave conditions, e.g. where the magnetostrictive element comprises a heat-sensitive polymer such as ABS. Preferably, the method includes coupling the magnetostrictive element to the velocity transducer by molding the magnetostrictive element from a mixture of a polymeric precursor and magnetostrictive particles onto the velocity transducer or onto a headpiece attachable to the velocity transducer.

One embodiment of the invention provides an ultrasonic dental appliance that includes a handpiece having an induction coil disposed about a well. The handpiece is operably connected to an adjustable power supply having a maximum output setting, and includes an insert. The insert has an efficiency-modulated magnetostrictive element adapted to be received in a well, a velocity transducer having proximal and distal ends, wherein the proximal end is attached to the distal end of the magnetostrictive element, and a power-sensitive tip operable in a power range. The power-sensitive tip has a proximal end secured to the distal end of the velocity transducer. The efficiency of the magnetostrictive element is matched to the power sensitivity of the tip to avoid overpowering the tip at the maximum power setting.

Another embodiment provides a method for adjusting power delivered to an ultrasonic insert in a handpiece having an induction coil disposed about a well and operably connected to an adjustable power supply having an adjustable power output setting ranging from a minimum to a maximum, wherein the insert comprises a power-sensitive tip having a power range. The method includes establishing an inventory of insert assemblies each comprising a tip, velocity transducer, and magnetostrictive element. The inventory comprises at least one insert assembly with a high-efficiency magnetostrictive element and a tip that is not power sensitive, and at least one insert assembly with an efficiency-modulated magnetostrictive element matched with a power-sensitive tip to maintain the tip within its power range at the maximum power output setting. The method can further include selecting one of the insert assemblies form the inventory, inserting the assembly in the well, supplying power to the induction coil, and adjusting the power output up to the maximum power output setting.

In one embodiment the selection of one of the insert assemblies can include coupling a power-sensitive tip to a velocity transducer operatively associated with an efficiency-modulated magnetostrictive element to maintain the power-sensitive tip within its power range at the maximum power output setting. The selection, insertion, power supplying, and adjustment can be repeated wherein the second selection comprises coupling a said tip that is not power-sensitive to a velocity transducer operatively associated with a said a high-efficiency magnetostrictive element.

Another embodiment of the present invention provides a method to distribute power-sensitive tips to dental practitioners for use in an insert assembly in a handpiece having an induction coil disposed about a well and operatively connected to an adjustable power supply having an adjustable power output setting with a maximum power output setting exceeding a power range of the tip. The method includes matching a power-sensitive tip for coupling to a velocity transducer and efficiency-modulated magnetostrictive element to form an insert assembly for use in the handpiece of at least one specified model of the adjustable power supply. The magnetostrictive element is efficiency modulated so that overpowering the tip is avoided at the maximum power output. The method further includes labeling the power-sensitive tip for use at full power range with the efficiency-modulated magnetostrictive element and the specified model of the adjustable power supply. The insert assembly can be assembled and provided to dental practitioners as a unit.

Another embodiment of the invention provides an improvement in a method of using different tips with a magnetostrictive element in an insert assembly in a handpiece having an induction coil disposed about a well and operably connected to an adjustable power supply having an adjustable power output setting with a maximum power output. A first one of the tips is power-sensitive and a maximum power output supplied to the first tip at or near peak resonant frequency needs to be modulated to avoid overpowering the tip, and a second one of the tips is not power sensitive, and no power modulation is needed to avoid overpowering the second tip at a maximum power setting. The improvement includes using the power-sensitive tip with an efficiency-modulated magnetostrictive element matched with the power range of the first tip so that overpowering the first tip is avoided at the maximum power output setting. The second tip that is not power sensitive can be used with a high-efficiency magnetostrictive element.

DETAILED DESCRIPTION

Figure 1:
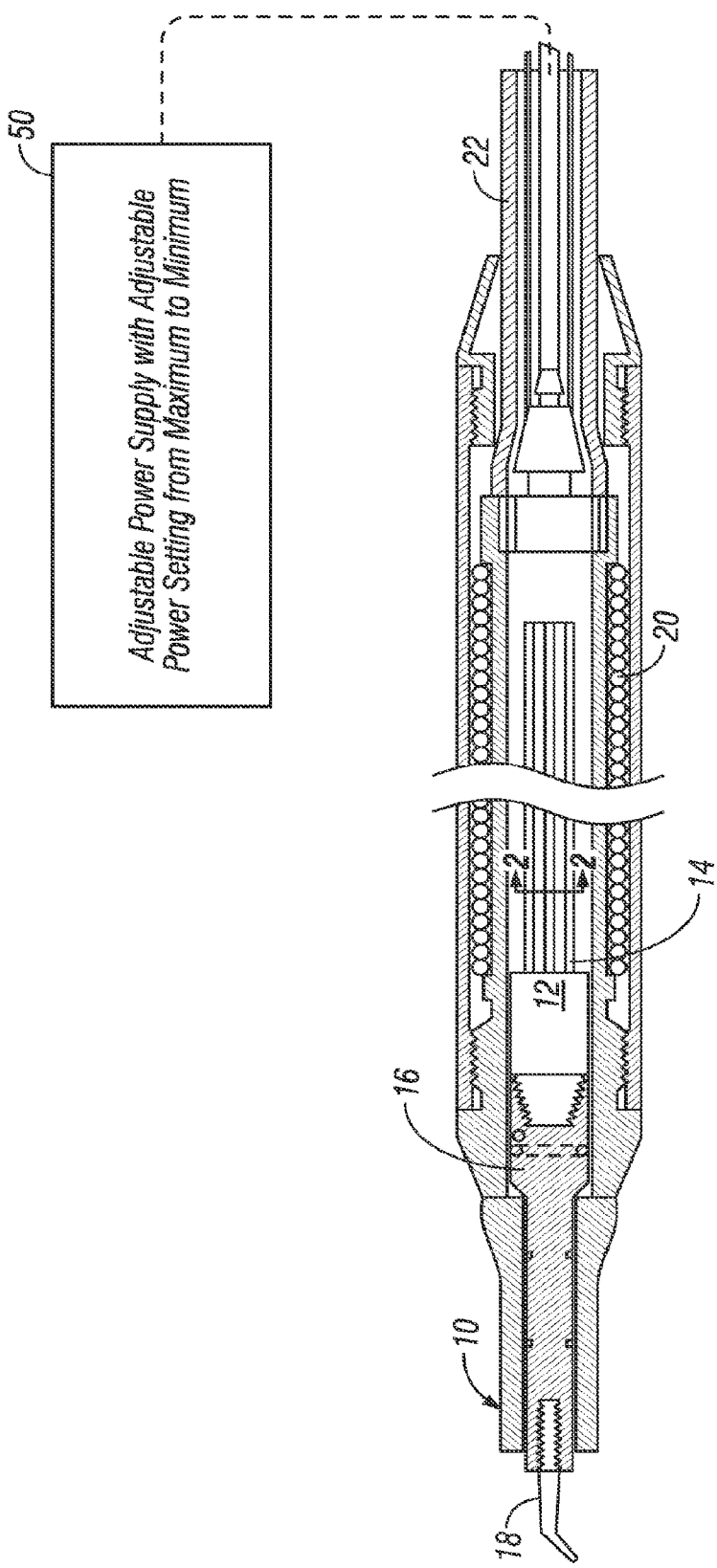
FIG. 1 is a side sectional view of an ultrasonic dental scaler according to one embodiment of the invention.

With reference to the figures wherein like reference numerals are used to refer to like parts, FIG. 1 shows the handpiece 10 receiving the insert 12 in a well known manner, e.g. by a friction fitting, which can generally be considered conventional in the art. The insert 12 includes a magnetostrictive element 14, velocity transducer 16 and power-sensitive tip 18. Briefly, the handpiece 10 has a well for receiving the insert 12 about which an inductive coil 20 is disposed for imposing an alternating magnetic field that oscillates the magnetostrictive element 14 at an ultrasonic frequency. The ultrasonic vibrations are transmitted from the magnetostrictive element 14 through the velocity transducer 16 and the tip 18, as is well known in the art. Electrical current from a power supply and control unit (not shown) is conventionally supplied to a proximal end of the handpiece 10 via the cable assembly 22.

Water is also supplied via the cable assembly 22 and cools the magnetostrictive element 14 as it passes through the well, in a manner well known in the art. The water then flows to the tip 18 where it serves to irrigate the working surface, for example, through a central channel (not shown) formed within the velocity transducer 16 or an outer groove or slot (not shown) that directs the water onto a base of the tip 18.

The power supply and control unit, shown in FIG. 1 in block diagram form as item 50, generally include resonance signal generation circuitry for producing a resonance signal received at the handpiece/insert via the cable. The control unit will also include a potentiometer or other means for adjusting the power sent to the handpiece, up or down, within minimum and maximum power output settings, for example, as a manual knob or dial on the control unit, a footswitch operably connected to the control unit, and/or a digital input device.

The magnetostrictive element 14 is efficiency modulated so that the conversion of electrical to mechanical energy is less efficient than in conventional handpieces. Preferably, the efficiency rating of the magnetostrictive element 14 is from 5 to 45 percent, more preferably from 15 to 35 percent, i.e. 5 to 45 or 15 to 35 percent of the electrical power output from the control unit is converted to mechanical vibratory energy at a peak power transfer point, typically 25 KHz or 30 KHz. The power range of the particular tip 18 is matched with the efficiency modulation of the magnetostrictive element 14 so that the tip 18 is not overpowered at the maximum power output setting of the control unit. This allows the operator to use the full range of power output adjustment without overstressing or otherwise overpowering the tip 18. The tip 18 can used for the full operating life of the insert without inadvertent metal fatigue tip breakage, and the power output can be adjusted by the operator to the desired setting with a greater degree of control.

The efficiency modulation of the magnetostrictive element 14 can be effected in a number of different ways. For example, the magnetostrictive element 14 can be conventional leaves made from a material such as nickel with less than optimum ultrasonic characteristics so that the standard stack configuration has less power transmittance. This lowers the power to the tip 18 without deviating from the operator's accepted concept of what a stack should look like, and without increasing the risk of damaging the stack by using fewer leaves that would result in a lowered mechanical integrity and dimensional stability.

Figure 2:
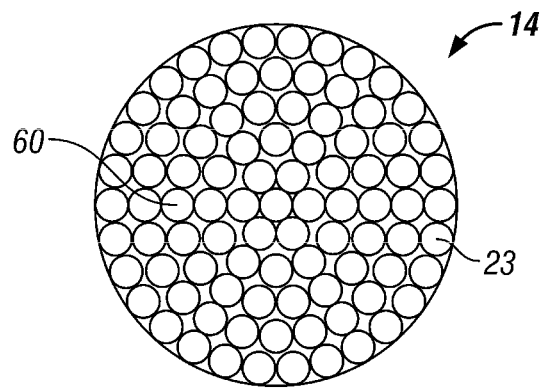
FIG. 2 is a cross-sectional view of a magnetostrictive element from the dental scaler of FIG. 1 comprising a plurality of longitudinal wires.
Figure 3:
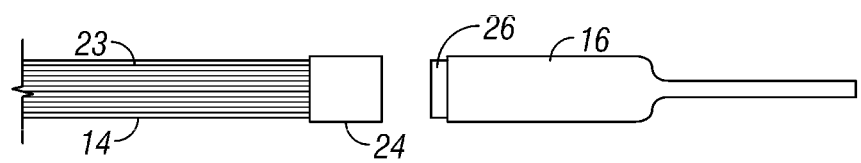
FIG. 3 is an exploded view of the ultrasonic insert of FIG. 1 according to one embodiment of the invention.

Another means for lowering the power can be achieved by changing the size and/or shape of the nickel. One example of this is seen in FIGS. 2-3 where longitudinally aligned nickel wires 23 are used in place of the conventional leaves. The stiffness of the stack is maintained, but less nickel is employed due to the void spaces between the wires. The relative proportion of the void spaces can be adjusted by varying the profile of the wires, i.e. the cross sectional shape, or by using wires of mixed outside diameters in the stack, for example 20 or 30 gauge wires randomly disposed about 16 or 14 gauge wires. The wires 23 can be secured by welding to the distal ring 24 using a silver solder that fluxes into the spaces between the wires adjacent the distal end thereof. The ring 24 is then welded to a proximal shoulder 26 of the velocity transducer 16 as shown in FIG. 3, or threadably connected as in FIG. 1.

Figure 4:
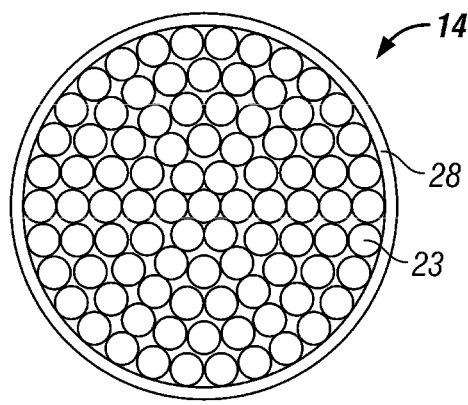
FIG. 4 is a cross-sectional view of another embodiment of the invention wherein the longitudinal wires are housed in an exterior nickel tube.
Figure 5:
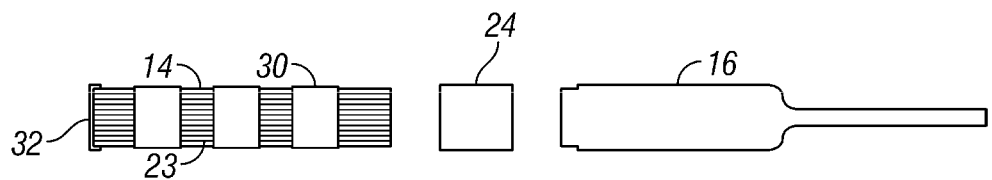
FIG. 5 is a side view, partly in section, of another embodiment of the invention including spaced containment rings and an end cap.
Figure 6:
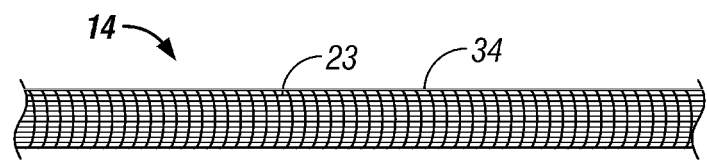
FIG. 6 is a perspective view of another embodiment of the invention wherein the longitudinal nickel wires are stiffened with a helical wire winding.

In FIG. 4 an external nickel tube 28 is employed to house the nickel wires 23 and impart stiffness to the stack. If desired, the tube can be another material such as aluminum, and/or surface anodized in various colors to differentiate and color code stacks with different characteristics. In FIG. 5, a plurality of longitudinally spaced containment rings 30 and end cap 32 are used to hold the wires 23 together and stiffen the stack. The rings 30 and end cap 32 can be a metal such as nickel that is silver brazed onto the stack. The rings 30 and end cap 32 can also be polymeric and secured by friction, adhesive, ultrasonic welding, heat-shrinking, or the like. In FIG. 6, the wires 23 are wrapped by a helically wound wire 34 to maintain the shape of the stack. The wire 34 can be nickel secured to the stack by brazing, tying or the like.

Figure 7:
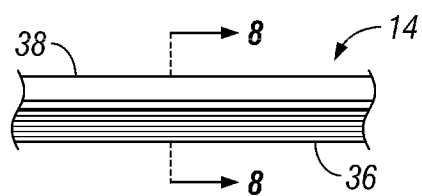
FIG. 7 is a side view of another embodiment of the invention wherein the stack includes a shaped nickel leaf to create a void in the magnetostrictive stack.
Figure 8:
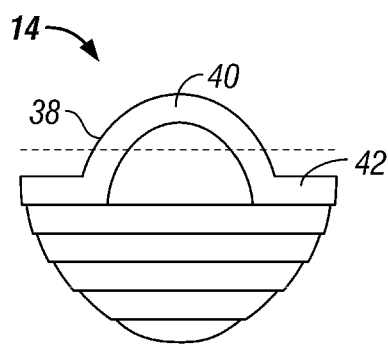
FIG. 8 is a cross-sectional view of the stack of FIG. 7 as seen along the lines 8-8.

FIGS. 7-8 illustrate an embodiment wherein a plurality of nickel conventional strips 36 in a stack is replaced with curvilinearly profiled strip 38 to reduce the amount of nickel or other magnetostrictive material present in the stack. The strip 18 has a cross section with a central semicylindrical region 40 and lateral ribs 42 on either side thereof. The profile of strip 38 also adds stiffness and rigidity to the stack.

Figure 9:
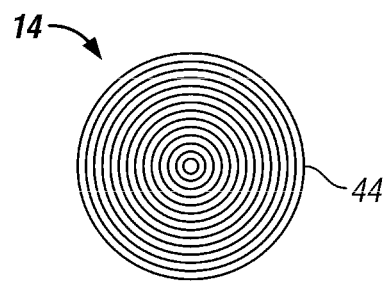
FIG. 9 is an end view of another embodiment of the invention wherein the stack comprises a plurality of nested tubes.

FIG. 9 shows another embodiment wherein concentric tubes 44 of various diameters are used to form the stack.

Another efficiency modulation embodiment according to the present invention is the use of a magnetostrictively inert material and/or a material in the stack bundle that would cause the RF field of the handpiece coil 20 to be shunted. For example, replacing one or more of the nickel wires or leaves with stainless steel wire 60 (see FIG. 2) or strips would lower the power available to the magnetostrictive components and lower the power to the tip.

Figure 10:
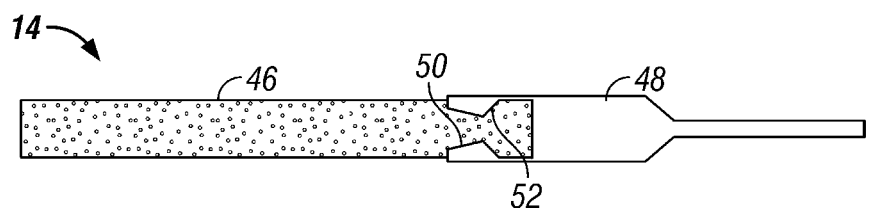
FIG. 10 is a side sectional view of a nickel particulate-filled polymeric monolith interlockingly molded to a velocity transducer.

FIG. 10 illustrates an embodiment wherein the magnetostrictive element 46 is made from a filled resin such as epoxy or ABS. The fill comprises nickel or another magnetostrictive material in particulated form that is maintained in its shape by a thermosetting or thermoplastic polymeric matrix. In FIG. 10 the magnetostrictive element 46 is molded directly to the proximal end of the velocity transducer 48 placed at one end of the mold (not shown). The velocity transducer 48 includes a neck 50 and an enlarged inner portion 52 that is filled with a mixture of nickel particles dispersed in a conventional polymer precursor during molding. When the polymer matrix is set in place, the formed stack 46 is thus secured to the velocity transducer 48. Alternatively or additionally, the velocity transducer can include a male coupling member (not shown) extending into the stack 46 as an anchor for coupling the velocity transducer and the magnetostrictive element together.

Figure 11:
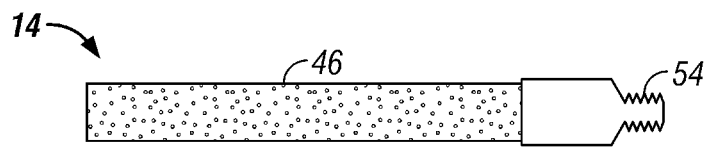
FIG. 11 is a side sectional view of a nickel particulate-filled monolith polymeric interlockingly molded to a headpiece for threadably coupling to the velocity transducer.

FIG. 11 shows a variation to the FIG. 10 embodiment wherein the stack 46 is molded onto a headpiece 54 having a threaded distal end for releasable attachment to a correspondingly threaded velocity transducer (not shown).

The embodiments of FIGS. 10-11 facilitate rapid and inexpensive stack fabrication. Further, they also allow the stack to be color coded by coloring the polymer matrix, or by printing or embossing printed information on an exterior surface. The manufacturer can thus use different colors or other visual indicia to code the stack for identifying different levels of efficiency modulation or other differentiating characteristics or specifications. If desired, the assembled insert 12 from the embodiments of FIGS. 10-11 can be packaged for a single use application. The insert 12 can be packaged in a sterilizable packaging for gas or irradiation sterilization. Where the product is gas sterilized, it is packaged in a gas permeable package that facilitates sterilization with ethylene oxide. Where gamma ray irradiation is used, the package containing the assembly should be transparent to gamma radiation.

This scheme can use different aspects of each of the various embodiments to tailor the stack characteristics to the type and performance of the tip. Of course, the handpiece (other than the insert) is not modified in the preferred embodiments of this invention, and the dental practitioner can thus continue to use the control unit and handpiece universally and interchangeably with conventional tips and inserts otherwise designed for the unit, as well as with the inserts of the present invention, without making any special adjustments to the unit and still allowing use of the full range of power output settings from the minimum to the maximum.

The power-sensitive tips 18 can be distributed to dental practitioners for use in an insert assembly, where the maximum power output setting of the adjustable power supply would normally exceed the power range of the tip 18 when used in an insert with a high-efficiency magnetostrictive element. In this invention, the power-sensitive tip 18 is matched to an efficiency-modulated magnetostrictive element 14, with a decreased efficiency of power conversion in comparison to the high-efficiency magnetostrictive elements. The tip 18 can thus be operated at the maximum setting of the power supply while maintaining the tip 18 within its power range, preventing overpowering of the tip 18.

The tip 18 can be labeled for use at a full power range, when used in combination with the efficiency-modulated magnetostrictive element 14 and the specified model of adjustable power supply. The power-sensitive tip 18 can also, if desired, be labeled for use at a reduced power setting when used in combination with a high-efficiency magnetostrictive element 14 and the specified model of adjustable power supply. As used herein, labeling can include traditional package or package insert labeling, but can also include other means of publishing the label information to the dental practitioner, such as, for example, presenting the information in catalogs, user manuals, website postings, and so on.

The power-sensitive tip and efficiency-modulated magnetostrictive element can be distributed separately with appropriate labeling to match the tip with an appropriate magnetostrictive element, or can be assembled together for distribution to dental practitioners as a unit. Providing a pre-assembled unit can have the advantage of helping to avoid mismatching a power-sensitive tip with a high-efficiency magnetostrictive element, or a tip that is not power sensitive with an efficiency-modulated magnetostrictive element. On the other hand, separate distribution of the tips and inserts can allow replacement of the tips when worn or damaged, for example, and provides the dental practitioner with the flexibility of interchanging different types of tips and/or magnetostrictive elements as desired.

While the invention has been described with respect to a limited number of embodiments, those skilled in the art will appreciate numerous modifications and variations therefrom. It is intended that the appended claims cover all such modifications and variations as fall within the true spirit and scope of the invention.

What is claimed is:

1. A method for adjusting power delivered to use different types of tips in ultrasonic dental inserts in a handpiece having an induction coil disposed about a well and operably connected to an adjustable power supply having an adjustable power output setting ranging from a minimum to a maximum, wherein the different tips comprise at least one power-sensitive tip having a power range, the method comprising:
    establishing an inventory of insert assemblies each comprising a tip, a velocity transducer and a magnetostrictive element, wherein the inventory comprises a first insert assembly with a high-efficiency magnetostrictive element and a tip that is not power sensitive and a second insert assembly with an efficiency-modulated magnetostrictive element matched with a power-sensitive type tip to maintain the matched power-sensitive type tip within the power range of the matched power-sensitive type tip at the maximum power output setting;
    wherein the high-efficiency magnetostrictive element is capable of converting 50% or more of an electrical power input to mechanical oscillatory power at a peak resonant frequency, and wherein the efficiency-modulated magnetostrictive element has a power conversion at the peak resonant frequency of less than 50% conversion of the electrical power input to mechanical oscillatory power;
    selecting one of the first or second insert assemblies from the inventory;
    inserting the selected assembly in the well;
    supplying power to the induction coil; and
    adjusting the power output up to the maximum power output setting.

2. The method of claim 1, wherein the efficiency-modulated magnetostrictive element comprises nickel.

3. The method of claim 1, wherein the efficiency-modulated magnetostrictive element comprises a plurality of coextensive longitudinally oriented nickel or nickel alloy wires having circular cross sections.

4. The method of claim 3, wherein the wires are welded at a distal end thereof inside a ring secured to the proximal end of the velocity transducer.

5. The method of claim 3, wherein the wires have uniform cross sections.

6. The method of claim 3, wherein the wires have non-uniform cross sections.

7. The method of claim 3, wherein the efficiency-modulated magnetostrictive element further includes one or more non-magnetostrictive wires.

8. The method of claim 3, wherein the efficiency-modulated magnetostrictive element further includes one or more magnetostrictive-dampening wires.

9. The method of claim 1, wherein the efficiency-modulated magnetostrictive element includes void space.

10. The method of claim 1, wherein the efficiency-modulated magnetostrictive element comprises a nickel rod.

11. The method of claim 1, wherein the efficiency-modulated magnetostrictive element includes a volume of non-magnetostrictive material.

12. The method of claim 1, wherein the selection further comprises coupling said matched power-sensitive type tip to a velocity transducer operatively associated with said efficiency-modulated magnetostrictive element to maintain said matched power-sensitive type tip within said power range of the matched power-sensitive type tip at the maximum power output setting.

13. The method of claim 12, further comprising a second selection comprising repeating the selection, insertion, power supplying and adjustment a second time wherein the second selection comprises coupling said tip that is not power-sensitive to a velocity transducer operatively associated with said high-efficiency magnetostrictive element.

14. A method for adjusting power delivered to use different types of tips in ultrasonic dental inserts in a handpiece having an induction coil disposed about a well and operably connected to an adjustable power supply having an adjustable power output setting ranging from a minimum to a maximum, wherein the different tips comprise at least one power-sensitive tip having a power range, the method comprising:

establishing an inventory of insert assemblies each comprising a tip, a velocity transducer and a magnetostrictive element, wherein the inventory comprises a first insert assembly with a high-efficiency magnetostrictive element and a tip that is not power sensitive and a second insert assembly with an efficiency-modulated magnetostrictive element matched with a power-sensitive type tip to maintain the matched power-sensitive type tip within the power range of the matched power-sensitive type tip at the maximum power output setting;

wherein the high-efficiency magnetostrictive element is capable of converting 50% or more of an electrical power input to mechanical oscillatory power at a peak resonant frequency, and wherein the efficiency-modulated magnetostrictive element has a power conversion at the peak resonant frequency of less than 50% conversion of the electrical power input to mechanical oscillatory power;

selecting one of the first or second insert assemblies from the inventory;

inserting the selected assembly in the well;

supplying power to the induction coil;

adjusting the power output up to the maximum power output setting; the method further comprising:

matching one of the at least one power-sensitive type tips for coupling to the velocity transducer and the efficiency-modulated magnetostrictive element to form the second insert assembly for use in the handpiece of a specified model of the adjustable power supply, wherein the magnetostrictive element is efficiency modulated so that overpowering the matched power-sensitive type tip is avoided at the maximum power output;

labeling the matched power-sensitive type tip for use at full power range with the efficiency-modulated magnetostrictive element and the specified model of the adjustable power supply; and distributing the second insert assembly with the efficiency-modulated magnetostrictive element to a dental practitioner.

15. The method of claim 14, further comprising labeling the matched power-sensitive type tip for use at a reduced power range setting with a high efficiency magnetostrictive element and the specified model of the adjustable power supply.

16. The method of claim 14, further comprising assembling the insert assembly with the efficiency-modulated magnetostrictive element and providing the insert assembly to the dental practitioner as a unit.

* * * * *